United States Patent
Berner

[11] 3,986,390
[45] Oct. 19, 1976

[54] APPARATUS FOR ULTRASONIC TESTING OF MARGINAL PORTIONS OF METALLIC SHEETS OR THE LIKE

[76] Inventor: Klaus Berner, Stromtal 89, Salzgitter-Lebenstedt, Germany

[22] Filed: Dec. 22, 1975

[21] Appl. No.: 642,991

Related U.S. Application Data

[63] Continuation of Ser. No. 489,948, July 18, 1974, abandoned.

[30] Foreign Application Priority Data
July 27, 1973 Germany............................ 275124

[52] U.S. Cl............................... 71.5 US; 73/67.8 S
[51] Int. Cl.².......................................... G01N 29/04
[58] Field of Search........... 73/67.5 R, 67.6, 67.8 R, 73/67.8 S, 67.9, 71.5 US

[56] References Cited
UNITED STATES PATENTS

| | | | |
|---|---|---|---|
| 3,055,210 | 9/1962 | Joy................................. | 73/71.5 US |
| 3,327,523 | 6/1967 | Kelemencky.................. | 73/71.5 US |
| 3,423,991 | 1/1969 | Collins............................ | 73/67.5 R |
| 3,670,562 | 6/1972 | Muto et al. .................... | 73/71.5 US |
| 3,929,007 | 12/1975 | Dent et al........................ | 73/67.8 S |

FOREIGN PATENTS OR APPLICATIONS

| | | | |
|---|---|---|---|
| 1,595,826 | 7/1970 | France............................. | 73/67.8 S |

*Primary Examiner*—Richard C. Queisser
*Assistant Examiner*—John P. Beauchamp
*Attorney, Agent, or Firm*—Michael J. Striker

[57] ABSTRACT

An ultrasonic testing apparatus which is mounted on the housing of a trimming device for one marginal portion of a sheet- or band-like workpiece moving lengthwise along a horizontal path. The testing apparatus has a deflector which is pivotably mounted on the housing by a hinge so that it can turn about a vertical axis and has ways for a pneumatic cylinder and piston assembly whose piston rod carries a roller follower movable at right angles to the path toward and away from engagement with one side of that marginal portion of a workpiece in the horizontal path which is about to be trimmed by the trimming device. The probe holder with the probe of the testing apparatus is mounted on a parallel motion mechanism which is carried by the piston rod and is biased by a spring so as to maintain the probe close to the one side of the one marginal portion of a moving workpiece when the latter is engaged by the roller follower. A spring automatically retracts the piston rod from the path in the event of malfunction of the cylinder and piston assembly, and the parallel motion mechanism carries a nozzle which discharges streams of compressed air serving to blow a liquid couplant off the one side of the workpiece downstream of the probe.

12 Claims, 3 Drawing Figures

APPARATUS FOR ULTRASONIC TESTING OF MARGINAL PORTIONS OF METALLIC SHEETS OR THE LIKE

This is a continuation, of application Ser. No. 489,948, filed July 18, 1974 now abandoned.

BACKGROUND OF THE INVENTION

The present invention relates to improvements in apparatus for ultrasonic non-destructive testing of elongated workpieces, such as metal sheets or bands, and more particularly to improvements in apparatus for ultrasonic testing of marginal portions of band- or sheet-like workpieces. The apparatus of the present invention is used for the testing of marginal portions of bandlike metallic workpieces while the workpieces move lengthwise on a roller table or the like.

It is already known to install an ultrasonic testing apparatus with one or more probes directly on the housing or frame of a trimming device or shears which trims one marginalportion of a moving band or sheet of metallic material. The probe is mounted on a parallel motion mechanism which is attached to the housing of the trimming device. As a rule, the probe is positioned to scan the workpiece along that line where the workpiece is to be trimmed. The parallel motion mechanism is deformable by a horizontally mounted fluid-operated cylinder and piston assembly which can cause the mechanism to move the probe up or down, i.e., toward or away from the path of workpieces. Such an assembly is disclosed, for example, in the German technical journal "Materialprufung" 7 (1965) 8, pp. 296-303.

The just described testing apparatus exhibits several serious drawbacks. Thus, the parallel motion mechanism is extremely bulky because it should be capable of moving the probe to a position at a considerable distance from the workpieces. Moreover, and when the probe is adjacent to a workpiece, it cannot yield in response to engagement with an oncoming protuberance so that it is often subjected to several mechanical stresses. Still further, the parallel motion mechanism is installed in a plane which is parallel to the direction of movement of workpieces so that it remains in the space above the path for the workpieces even when the probe is lifted. Therefore, the parallel motion mechanism interferes with access to the probe and/or with access to the conveying means for workpieces below the testing station. This complicates the task of repairmen and causes prolonged interruptions in operation of the testing apparatus and trimming device whenever a component part at the testing station necessitates inspection, adjustment or replacement.

SUMMARY OF THE INVENTION

An object of the invention is to provide an apparatus for ultrasonic testing of marginal portions of metallic sheets or bands which is simpler and more compact than heretofore known apparatus, which affords convenient access to its components, and which enables the probe or probes to yield in response to engagement with oncoming protuberances of workpieces so that the wear upon and the likelihood of damage to the probe or probes is less pronounced than in heretofore known apparatus.

Another object of the invention is to provide novel and improved means for moving one or more probes and the parallel motion mechanism(s) for the probe(s) with respect to the path for sheet- or band-like metallic workpieces.

A further object of the invention is to provide an ultrasonic margin tester for metallic sheets or bands which can be mounted on existing shears for such workpieces.

The invention resides in a combination of the housing of a trimming device for a marginal portion of an elongated sheet- or band-like workpiece which is transported lengthwise in a predetermined direction and along a predetermined path (preferably along a horizontal path) toward, past and beyond the trimming device with a novel and improved ultrasonic testing apparatus which includes a deflector mounted on the housing of the trimming device and extending close to one side of a marginal portion of a workpiece in the path so that the deflector is located ahead of the housing, as considered in the direction of lengthwise movement of workpieces toward the trimming device, a fluid-operated cylinder and piston assembly which is mounted on the deflector and has a portion (such portion may include a piston rod and at least one roller follower on the piston rod) reciprocable substantially at right angles to the direction of movement of workpieces into and from engagement with the one side of the one marginal portion of a workpiece in the path, a parallel motion mechanism which is mounted on the movable portion of the cylinder and piston assembly, at least one ultrasonic probe mounted on the parallel motion mechanism, and a helical spring or analogous means for yieldably biasing the parallel motion mechanism (i.e., for deforming the mechanism) so as to maintain the probe in close proximity of the path when the movable portion of the cylinder and piston assembly engages a workpiece.

The probe holder is preferably articulately connected with the parallel motion mechanism, e.g., by a cardan joint or another suitable universal joint. The deflector preferably comprises guide means or ways for the cylinder and piston assembly, and the deflector is preferably secured to the housing of the trimming device by a hinge which enables the deflector and the cylinder and piston assembly to turn about an axis which is normal to the path for workpieces, i.e., about a vertical axis if the workpieces are transported along a horizontal path.

The novel features which are considered as characteristic of the invention are set forth in particular in the appended claims. The improved testing apparatus itself, however, both as to its construction and its mode of operation, together with additional features and advantages thereof, will best be understood upon perusal of the following detailed description of certain specific embodiments with reference to the accompanying drawing.

DESCRIPTION OF THE PREFERRED EMBODIMENTS

Figure 1:
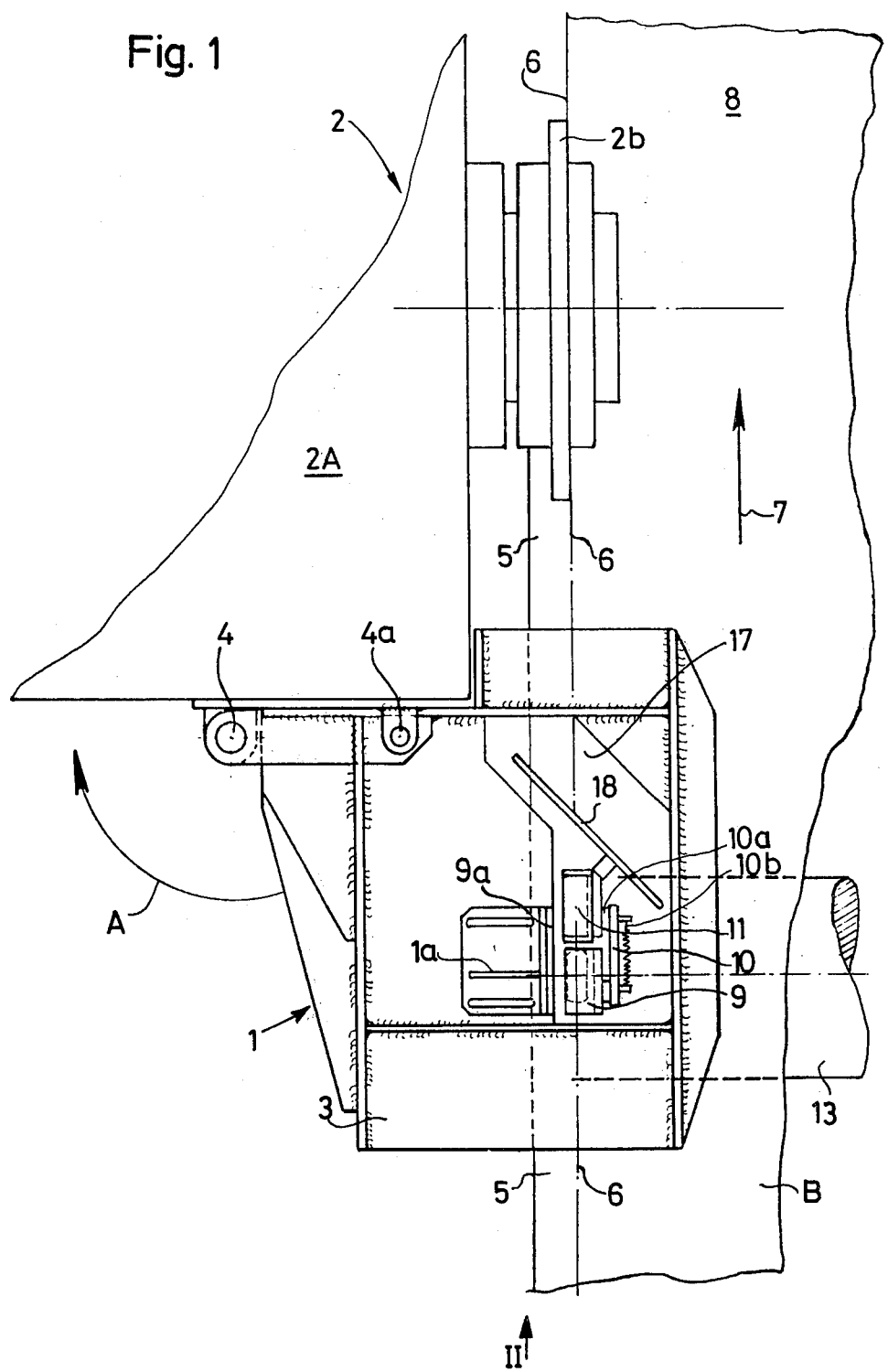
FIG. 1 is a plan view of a trimming device and an ultrasonic testing apparatus which embodies the invention.
Figure 2:
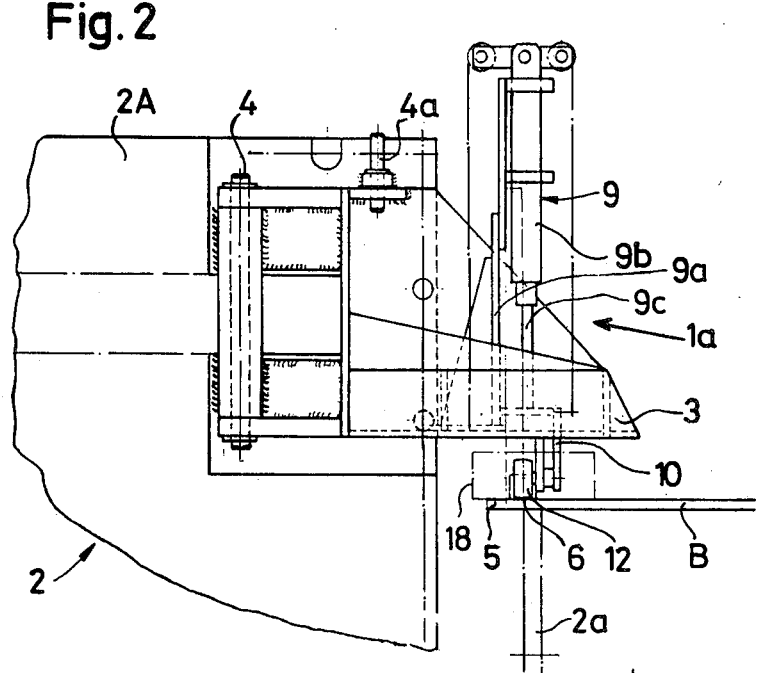
FIG. 2 is a view as seen in the direction of arrow II in FIG. 1.
Figure 3:
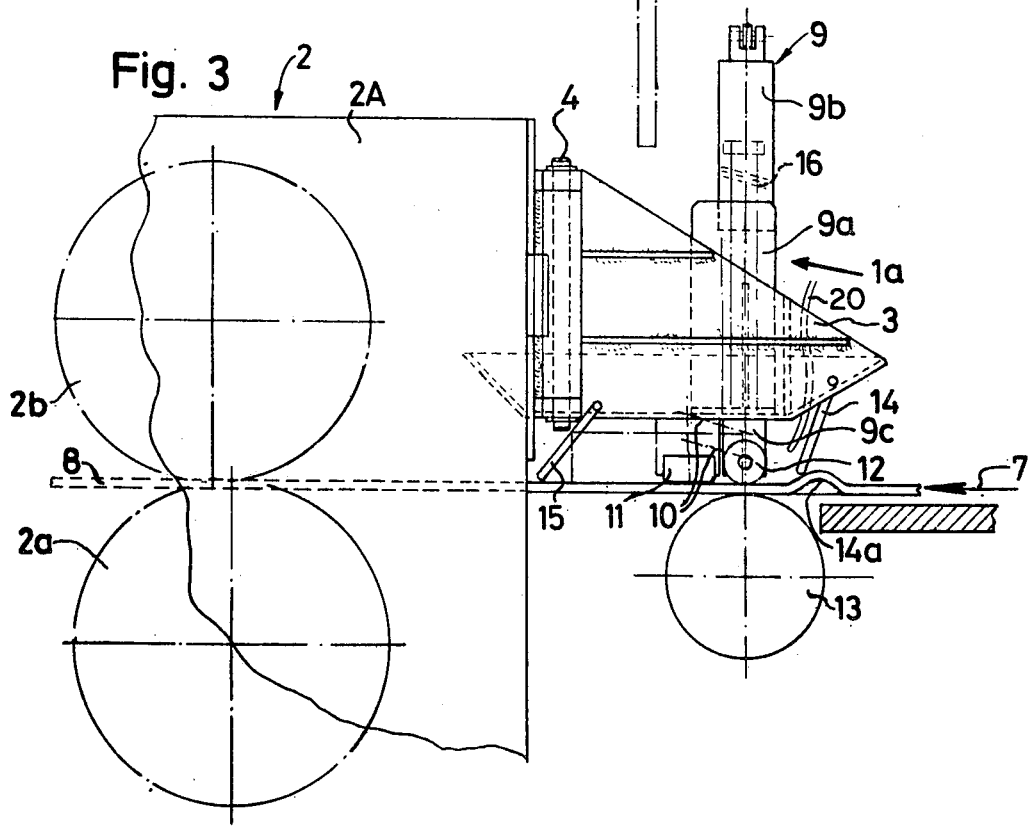
FIG. 3 is an elevational view as seen from the left-hand side of FIG. 1.

FIGS. 1 to 3 show an apparatus 1 for ultrasonic testing of marginal portions of workpieces in the form of sheets or bands B. This apparatus is installed adjacent to the path of workpieces B and ahead of a trimming device or shears 2 serving to sever the workpiece along a line 6, i.e., to remove a narrow strip 5. The direction in which the workpiece B is transported toward, past and beyond the apparatus 1 and shears 2 is indicated by arrow 7. The trimmed workpiece is shown at 8.

The testing apparatus 1 comprises a unit 1a which includes a probe holder 11 and means for moving the probe up and down. This unit is separably secured to a deflector 3 which is pivotable on or with an upright pintle 4 forming part of a hinge. The latter is mounted on the housing 2A of the shears 2 and the deflector 3 is separably mounted thereon. A bolt 4a or the like can be provided to releasably lock the deflector 3 in its operative position.

The means for moving the probe holder 11 up and down comprises a fluid-operated cylinder and piston assembly 9 whose piston rod 9c is guided by vertical ways 9a on the deflector 3 and carries at its lower end a roller follower 12 normally engaging the upper side of a marginal portion of the workpiece B. The piston rod 9c of the assembly 9 further carries a parallel motion mechanism 10 which is biased by a spring 10b so that it tends to maintain the probe holder 11 in close proximity of the upper side of the workpiece B. The probe holder 11 is secured to the mechanism 10 by a universal joint 10a and includes at least one testing head of conventional design (cf. Report C-04 of the VII ICNDT, Warsaw (Poland), 408 June 1973). When the piston rod 9c of the assembly 9 is lifted, the mechanism 10 moves the probe holder 11 upwardly and away from the path for the workpiece B.

The underside of the deflector 3 carries two detectors 14, 15 which are respectively located upsteam and downstream of the probe holder 11 as considered in the direction of movement of a workpiece B. The detector 15 produces a signal for example over an electric switch or the like when it detects the leader of a workpiece, and the detector 14 produces a signal for example over an electric switch or the like in response to detection of the trailing end of a workpiece. Furthermore, the detectors 14, 15 can react in response to detection of unevennesses (e.g., humps 14a) at the upper side of a workpiece B. The signals which are furnished by the detector 14 actuate for example over a valve controlled by the signals which is placed in the actuating circuit of the assembly 9, the assembly 9 in such a way that the probe holder 11 rises in response to detection of a hump 14a or the trailing end of a workpiece B. The detector 15 monitors the adjacent edge of the workpiece B and lowers the probe holder 11 in response to detection of the leader of a workpiece.

A resetting spring 16 is provided to permanently urge the probe holder 11 away from the path of workpieces. This spring becomes effective when the assembly 9 is out of commission and is especially desirable if the cylinder 9b of the assembly 9 is normally connected with a source of compressed gaseous fluid. FIG. 1 shows that the deflector 3 has a cutout 17 which is large enough to allow the mechanism 10 with probe holder 11 and roller follower 12 to move up or down. The mechanism 10 further carries an elongated nozzle 18 having orifices which discharge streams of compressed air to blow away the liquid couplant from the upper side of a workpiece. The liquid couplant is supplied to the upper side of the workpiece through a conduit 20 having an outlet end upstream of the probe holder, as considered in the direction of travel of the travelling material B.

The means for conveying workpieces B along a preferably horizontal path comprises several sets of driven rolls or drums one of which is shown in FIG. 3, as at 13.

The operation:

When the probe holder 11 is lifted above and away from the path for workpieces B, a workpiece can be readily introduced into the path defined in part by the rolls 13. As the leader of a fresh workpiece B engages the detector 15, the latter changes its position and actuates the cylinder and piston assembly 9 so that the probe holder 11 descends until the roller follower 12 engages and begins to track the upper side of the workpiece. The probe holder 11 can engage the upper side of the workpiece but is readily yieldable because it is mounted on the parallel motion mechanism 10 and is biased against the workpiece by the spring 10b.

The probe tests the workpiece B along the line 6, i.e., along the edge of the band or sheet 8 which is obtained in response to trimming of the workpiece by the knives 2a, 2b of the shears 2. If the device 14 detects an unevenness (such as the hump 14a shown in FIG. 3) or the trailing end of a workpiece B, the assembly 9 is actuated to lift the probe holder 11 above and away from the path for workpieces. This insures that humps or the like cannot damage the probe as well as that the probe remains lifted and affords convenient access to the path for workpieces when the path portion below the roller follower 12 is empty.

It will be readily appreciated that a workpiece B is normally tested by two apparatus 1 of the type shown in FIGS. 1–3, i.e., that the means for trimming and testing of workpieces comprises two shears 2 (each adjacent to one marginal portion of a workpiece B) and two testing apparatus 1 each of which is mounted ahead of one of the shears 2.

The piston rod 9c of the assembly 9 can carry two or more roller followers 12. The assembly 9 is preferably operated by compressed air.

The deflector 3 constitutes with the assembly 9 and with the parts which are mounted on the assembly 9 a first module which is separably mounted on the housing 2A of the trimming device 2, and the assembly 9 constitutes with the mechanism 10 and probe holder 11 a second module which is separable from the deflector 3. This facilitates the dismantling and renders it possible to rapidly replace a defective module and/or to inspect a removed module with little loss in time.

The deflector 3 constitutes a first safety device which shields the probe against excessive stresses. Since the assembly 9 is preferably operated with compressed air, its piston 9c and the roller follower 12 constitute a second safety device which can yield when the follower 12 is engaged by an oncoming protuberance. The piston rod 9c of the assembly 9 normally urges the parallel motion mechanism 10 toward the workpiece B with a constant force, and the mechanism 10 constitutes a further safety device which enables the probe holder 11 to yield (when necessary) while the axial position of the piston rod 9c of the assembly 9 remains unchanged. A parallel motion mechanism (together with suitable biasing means therefor) which can be mounted on the piston rod 9c of the assembly 9 is described in detail in the commonly owned copending application Ser. No. 489,950 filed July 18, 1974 by Berner et al, now U.S. Pat. No. 3,913,388. Reference may be had to FIGS. 6–8 of the said copending application.

The combined weight of the piston rod 9c of the assembly 9, of the mechanism 10, and of the probe holder 11 is relatively small so that such parts can be rapidly lifted or lowered by resorting to a relatively small pneumatic cylinder 9b and by operating with small quantities of compressed air.

The bolt 4a will be removed so that the deflector 3 can be pivoted about the axis of the pintle 4 when the attendants wish to move the testing apparatus to one side of the path for the workpieces B. In such inoperative position of the testing apparatus, its modules and/or discrete components are readily accessible for detachment from the housing 2A of the trimming device or for inspection. Also, such pivoting of the testing apparatus in a counterclockwise direction (see the arrow A in FIG. 1) enables the attendants to inspect the conveyor system for workpieces, to inspect the workpieces, and/or to gain access to the knives 2a, 2b of the trimming device 2.

The spring 16 automatically lifts the probe holder 11 above and away from the path for workpieces in the event of malfunction of the assembly 9.

Liquid couplant is fed into the gap between the probe and the upper side of a workpiece B therebelow. The couplant is blown away by gaseous fluid issuing from the orifices of the nozzle 18. Such fluid can be supplied by the source which is associated with the cylinder and piston assembly 9.

Without further analysis, the foregoing will so fully reveal the gist of the present invention that others can, by applying current knowledge, readily adapt it for various applications without omitting features which fairly constitute essential characteristics of the generic and specific aspects of my contribution to the art and, therefore, such adaptations should and are intended to be comprehended within the meaning and range of equivalence of the claims.

What is claimed as new and desired to be protected by Letters Patent is set forth in the appended claims.

I claim:

1. In combination with a trimming device for a marginal portion of elongated sheet- or band-like material travelling along a predetermined path towards the trimming device, an ultrasonic testing apparatus including a follower riding on the travelling material, a cylinder-and-piston unit comprised of a cylinder portion and a piston portion, one of the portions being reciprocable generally normal to the travelling material and being furthermore supported on the follower so as to rise and descend in response to travel of elevated and depressed portions of the material past and beneath the follower, a parallel-motion mechanism supported on the reciprocable portion, a probe holder located downstream of the follower and supported on the parallel-motion mechanism and mounted by the latter for movement relative to the reciprocable portion in direction toward and away from the travelling material, and biasing means biasing the parallel-motion mechanism in a direction urging the probe holder toward the travelling material, the follower and the reciprocable portion of the cylinder-and-piston unit together serving to properly position the probe holder relative to the travelling material during passage beneath the follower of relatively long-stretch rises or depressions in the travelling material, the parallel-motion mechanism and the biasing means serving to properly position the probe holder relative to the travelling material during passage beneath the follower of relatively short-stretch rises or depressions in the travelling material.

2. The combination defined in claim 1, the follower being a roller.

3. The combination defined in claim 1, the ultrasonic testing apparatus further including a deflector mounted on the trimming device and extending in upstream direction in the region of the marginal portion to be tested using the ultrasonic testing apparatus, the cylinder-and-piston unit being supported on the deflector.

4. The combination defined in claim 3, the deflector being mounted on the trimmer for pivoting movement about a pivot axis extending normal to the travelling material between an operative position and a swung-out inoperative position, and means for locking the deflector in the operative position.

5. The combination defined in claim 3, the ultrasonic testing apparatus furthermore including detectors located upstream and downstream of the probe holder and follower for generating control signals for the control of the cylinder-and-piston unit in response to detection of leading and trailing ends of travelling material and rises and depressions in the travelling sheet material.

6. The combination defined in claim 3, the ultrasonic testing apparatus furthermore including a detector located to detacts the leading end of the travelling material and generate control signal for causing the reciprocable portion of the cylinder-and-piston unit to move toward the travelling material.

7. The combination defined in claim 3, the ultrasonic testing apparatus furthermore including a detector located to detect the trailing end of the travelling material and generate a control signal for causing the reciprocable portion of the cylinder-and-piston unit to move away from the travelling material.

8. The combination defined in claim 1, the cylinder-and-piston unit including means for continually urging the reciprocable portion away from the travelling sheet material, whereby to effect retraction of the reciprocable portion in the event of malfunction of the cylinder-and-piston unit.

9. The combination defined in claim 1, further including a nozzle mounted on the reciprocable portion of the cylinder-and-piston unit and having orifices arranged to discharge streams of a gaseous fluid against one side of the travelling material.

10. The combination defined in claim 9, the nozzle being disposed between the cylinder-and-piston unit and the trimming device.

11. The combination defined in claim 9, liquid couplant being fed between the probe holder and one side of the travelling material, with the streams of gaseous fluid blowing the couplant off the travelling material as the latter advances from the probe holder towards the trimming device.

12. The combination defined in claim 3, the probe holder, parallel-motion mechanism, biasing means and cylinder-and-piston unit being removably mounted on the deflector as a single unit.

* * * * *

UNITED STATES PATENT AND TRADEMARK OFFICE
CERTIFICATE OF CORRECTION

PATENT NO. : 3,986,390
DATED : Oct. 19, 1976
INVENTOR(S) : Klaus Berner

It is certified that error appears in the above-identified patent and that said Letters Patent are hereby corrected as shown below:

[30] The serial number of the German application should read:

73 27 512

Signed and Sealed this

Fifteenth Day of March 1977

[SEAL]

Attest:

RUTH C. MASON
*Attesting Officer*

C. MARSHALL DANN
*Commissioner of Patents and Trademarks*